(12) United States Patent
Beaufore et al.

(10) Patent No.: US 7,306,586 B2
(45) Date of Patent: Dec. 11, 2007

(54) CONTINUOUS DRAINAGE ADAPTOR

(75) Inventors: Spencer W. Beaufore, Dublin, OH (US); Glenn D. Brunner, Dublin, OH (US)

(73) Assignee: OPMI Funding Corporation, Dublin, OH (US)

( * ) Notice: Subject to any disclaimer, the term of this patent is extended or adjusted under 35 U.S.C. 154(b) by 420 days.

(21) Appl. No.: 10/749,063

(22) Filed: Dec. 30, 2003

(65) Prior Publication Data

US 2005/0148999 A1    Jul. 7, 2005

(51) Int. Cl.
 *A61M 25/16* (2006.01)
(52) U.S. Cl. .................. 604/533; 604/244; 604/544
(58) Field of Classification Search ............ 604/544, 604/246–247, 256, 533–537, 164.01–164.13, 604/165.03, 905, 250, 178, 244; 600/29–32
See application file for complete search history.

(56) References Cited

U.S. PATENT DOCUMENTS

| | | | |
|---|---|---|---|
| 3,421,509 A | 1/1969 | Fiore ........................... | 604/171 |
| 4,195,632 A | 4/1980 | Parker et al. ................. | 128/272 |
| 4,362,156 A * | 12/1982 | Feller et al. ............ | 604/165.03 |
| 4,457,749 A | 7/1984 | Bellotti et al. ................. | 604/29 |
| 4,553,959 A | 11/1985 | Hickey et al. .......... | 604/103.09 |
| 4,643,389 A * | 2/1987 | Elson et al. .................... | 251/10 |
| 4,745,950 A * | 5/1988 | Mathieu ...................... | 137/798 |
| 4,752,287 A | 6/1988 | Kurtz et al. .............. | 604/99.02 |
| 4,795,426 A | 1/1989 | Jones ......................... | 604/539 |
| 4,946,449 A | 8/1990 | Davis, Jr. .................... | 604/256 |
| 5,035,399 A * | 7/1991 | Rantanen-Lee .............. | 251/10 |
| 5,270,003 A * | 12/1993 | Bernes et al. ................. | 422/44 |

(Continued)

FOREIGN PATENT DOCUMENTS

EP          0 795 342         9/1997

(Continued)

OTHER PUBLICATIONS

International Searching Authority, *Partial Search and Invitation to Pay Additional Fees*, PCT/US2004/036531, filed Feb. 11, 2004.

*Primary Examiner*—Nicholas Lucchesi
*Assistant Examiner*—Theodore J Stigell
(74) *Attorney, Agent, or Firm*—Wood, Herron & Evans, LLP (57) ABSTRACT

An adaptor 20 temporarily transforms a valved urinary catheter 2 into one that permits continuous fluid flow by deforming the valve 3. The adaptor 20 includes a tube 22 that sealingly engages into the catheter outlet tube 4 and is provided with an actuator member 24 extending therefrom that engages the catheter valve 3. The actuator member 24 is sized to allow urine to flow therearound and into the tube 22, when the member 24 extends into engagement with the valve to deformably open same. However, the actuator member 24 is of a smaller diameter than the tube 22, and therefore does not greatly deform the valve 3 thereby avoiding damage to the valve 3. The adaptor 20 additionally includes a releasable clip 30, 32 that augments the frictional fit between the outlet tube 4 of the catheter 2 and the adaptor 20. The clip 30, 32 can also be sized to interact with a portion of the catheter 2 or the valve housing 5 to ensure the adaptor 20 is inserted an appropriate distance into the catheter 2.

84 Claims, 2 Drawing Sheets

U.S. PATENT DOCUMENTS

| | | | |
|---|---|---|---|
| 5,306,226 A | 4/1994 | Salama | 600/29 |
| 5,456,284 A | 10/1995 | Ryan et al. | 137/522 |
| 5,484,401 A | 1/1996 | Rodriguez et al. | 604/28 |
| 5,603,685 A | 2/1997 | Tutrone, Jr. | 600/29 |
| 5,611,768 A | 3/1997 | Tutrone, Jr. | 600/29 |
| 5,624,395 A | 4/1997 | Mikhail et al. | 604/99.04 |
| 5,628,770 A | 5/1997 | Thome et al. | 607/101 |
| 5,645,528 A | 7/1997 | Thome | 604/96.01 |
| 5,707,357 A | 1/1998 | Mikhail et al. | 604/96 |
| 5,718,686 A | 2/1998 | Davis | 604/101.05 |
| 5,724,994 A | 3/1998 | Simon et al. | 128/885 |
| 5,785,641 A | 7/1998 | Davis | 600/30 |
| 5,785,694 A | 7/1998 | Cohen et al. | 604/250 |
| 5,800,339 A | 9/1998 | Salama | 600/29 |
| 5,951,519 A * | 9/1999 | Utterberg | 604/167.01 |
| 5,964,732 A | 10/1999 | Willard | 604/117 |
| 5,971,967 A | 10/1999 | Willard | 604/264 |
| 6,004,290 A | 12/1999 | Davis | 604/103.03 |
| 6,050,934 A | 4/2000 | Mikhail et al. | 600/30 |
| 6,162,201 A | 12/2000 | Cohen et al. | 604/250 |
| 6,167,886 B1 | 1/2001 | Engel et al. | 128/885 |
| 6,183,520 B1 | 2/2001 | Pintauro et al. | 623/23.64 |
| 6,193,697 B1 | 2/2001 | Jepson et al. | 604/201 |
| 6,213,996 B1 * | 4/2001 | Jepson et al. | 604/533 |
| 6,221,060 B1 | 4/2001 | Willard | 604/264 |
| 6,258,060 B1 | 7/2001 | Willard | 604/117 |
| 6,290,206 B1 * | 9/2001 | Doyle | 251/149.1 |
| 6,299,598 B1 | 10/2001 | Bander | 604/101.03 |
| RE37,704 E | 5/2002 | Eshel | 604/113 |
| 6,409,967 B1 | 6/2002 | McIntosh | 422/44 |
| 6,447,498 B1 | 9/2002 | Jepson et al. | 604/411 |
| 6,494,855 B2 | 12/2002 | Rioux et al. | 602/67 |
| 6,494,879 B2 | 12/2002 | Lennox et al. | 606/8 |
| 6,527,702 B2 | 3/2003 | Whalen et al. | 600/30 |
| 6,541,802 B2 | 4/2003 | Doyle | 251/149.1 |

FOREIGN PATENT DOCUMENTS

| | | |
|---|---|---|
| GB | 2 339 455 | 1/2000 |

* cited by examiner

CONTINUOUS DRAINAGE ADAPTOR

BACKGROUND OF THE INVENTION

I. Field of the Invention

The present invention relates generally to urinary flow control valves, and, more particularly, to adapting such valves to temporarily permit continuous fluid flow.

II. Description of Prior Art

Urinary control devices, such as urinary catheters, have been developed to facilitate bladder drainage in individuals who are unable to initiate or control such drainage for a variety of medical reasons. Two types of urinary catheters have been developed to assist in this need and can be considered as comprising either a continuous drainage catheter or a valved urinary catheter. Continuous drainage catheters are used when continuous drainage of an individual's bladder into a collection bag or reservoir is desired, such as during or after surgery or when mobility of the individual is not a primary concern. Valved urinary catheters, on the other hand, are used to retain urine within the bladder until it is desired to void the bladder through actuation of a normally-closed urinary flow control valve located within or external to the urethra. The urinary valves of such devices typically include a valve housing with flexible, resilient walls that contain therewithin the actual valve element. When the housing walls are squeezed either directly when the valve housing is outside of the urethra, or through palpitation through the penis, for example, when the valve housing is in the urethra, the walls flex and cause the valve therein to deform and open for release of urine. Release of the squeezing pressure on the housing walls allows the valve to return to its original, closed state.

Valved urinary catheters are used predominantly with mobile individuals so as to provide a urinary flow control device that is not discernable by others and that is compatible with the individual's normal daily activities. However, there are times when it is convenient for the valved urinary catheter to be temporarily configured to allow continuous flow. With such a capability, the benefits of both types of catheters can be achieved without requiring an individual to undergo removal of one type of catheter and insertion of the other. Previous attempts at addressing this problem involved inserting a hollow tube, roughly the size of the inside of the catheter tube, into the catheter outlet far enough to grossly deflect the valve and to cause the valve to open. The tube would form a fluid-tight seal between the walls of the catheter outlet and the outer surface of the hollow tube. As a result, urine can continuously flow through the inside of the hollow tube.

The prior approach has several shortcomings. By way of example, the tube has the tendency to greatly deform, and thereby damage, the valve during use, especially prolonged use. As a consequence, the valve may no longer be able to seal after the hollow tube is removed, leading to unacceptable leakage. Further, the tube is held in place only by frictional engagement which can often work loose resulting in leakage and/or failure of the valve to be held open.

SUMMARY OF THE INVENTION

The present invention provides an adaptor which temporarily transforms a valved urinary catheter into one that permits continuous fluid flow by deforming the valve in a manner similar to prior hollow tubes, but without the shortcomings thereof. To this end, and in accordance with one aspect of the present invention, the adaptor includes a tube which sealingly engages with the catheter outlet and also includes an actuator member having a tip sized to allow urine to flow therearound and into the tube when the actuator member extends against the downstream side of the valve to deformably open same. However, the actuator member is of a smaller diameter than the tube, and therefore does not greatly deform the valve, thereby overcoming one of the shortcomings of the use of prior hollow tubes as the structure for both fluid flow and for deforming and opening the valve.

As mentioned, another shortcoming of prior hollow tube approaches is that the tube may come loose. The present invention provides an adaptor which overcomes that shortcoming. To that end, and in accordance with this aspect of the present invention, a releasable clip is advantageously associated with the tube, the releasable clip adapted to engage with an exterior surface of the catheter outlet, so as to hold the adaptor in place with the member holding the valve body open for continuous flow. To this end, the clip may squeeze down on the outside of the catheter outlet to help maintain the seal with the tube of the adaptor. As a consequence, where the releasable clip is provided, the sealing engagement of the tube with the catheter outlet is not the sole source of hold so is not as likely to come loose and leak or allow the valve to unexpectedly close. The clip may include a safety feature that prevents it from being overly compressed against the catheter outlet. To prevent under-insertion of the adaptor within the catheter, the clip may be designed to engage an exterior surface of the catheter only when the adaptor is fully inserted. Additionally, the clip may include a protuberance that contacts an external portion of the catheter, valve housing, or discharge tube so as to prevent the adaptor from being over-inserted into the catheter.

In accordance with a yet further aspect of the present invention, the actuator member is advantageously solid, such that all urine flow is around the member and into the tube. However, increased fluid flow may be obtained by using a hollow actuator member, such that urine flows both around and through the member and into the tube. The member may advantageously be a pin or rod. Where the valve is a duckbill-like valve with an openable slit therein, the actuating member has a diameter smaller than the length of the slit such that when inserted against the valve, the slit will open to provide fluid flow regions between the actuating member and the walls of the duckbill valve slit.

By virtue of the foregoing, there is thus provided an adaptor which temporarily transforms a valved urinary catheter into one that permits continuous fluid flow by deforming the valve in a manner similar to prior hollow tubes, but without the shortcomings thereof. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention, and together with the general description of the invention given above, and the detailed description of the embodiments given below, serve to explain the principles of the present invention.

DETAILED DESCRIPTION OF THE DRAWINGS

Figure 1:
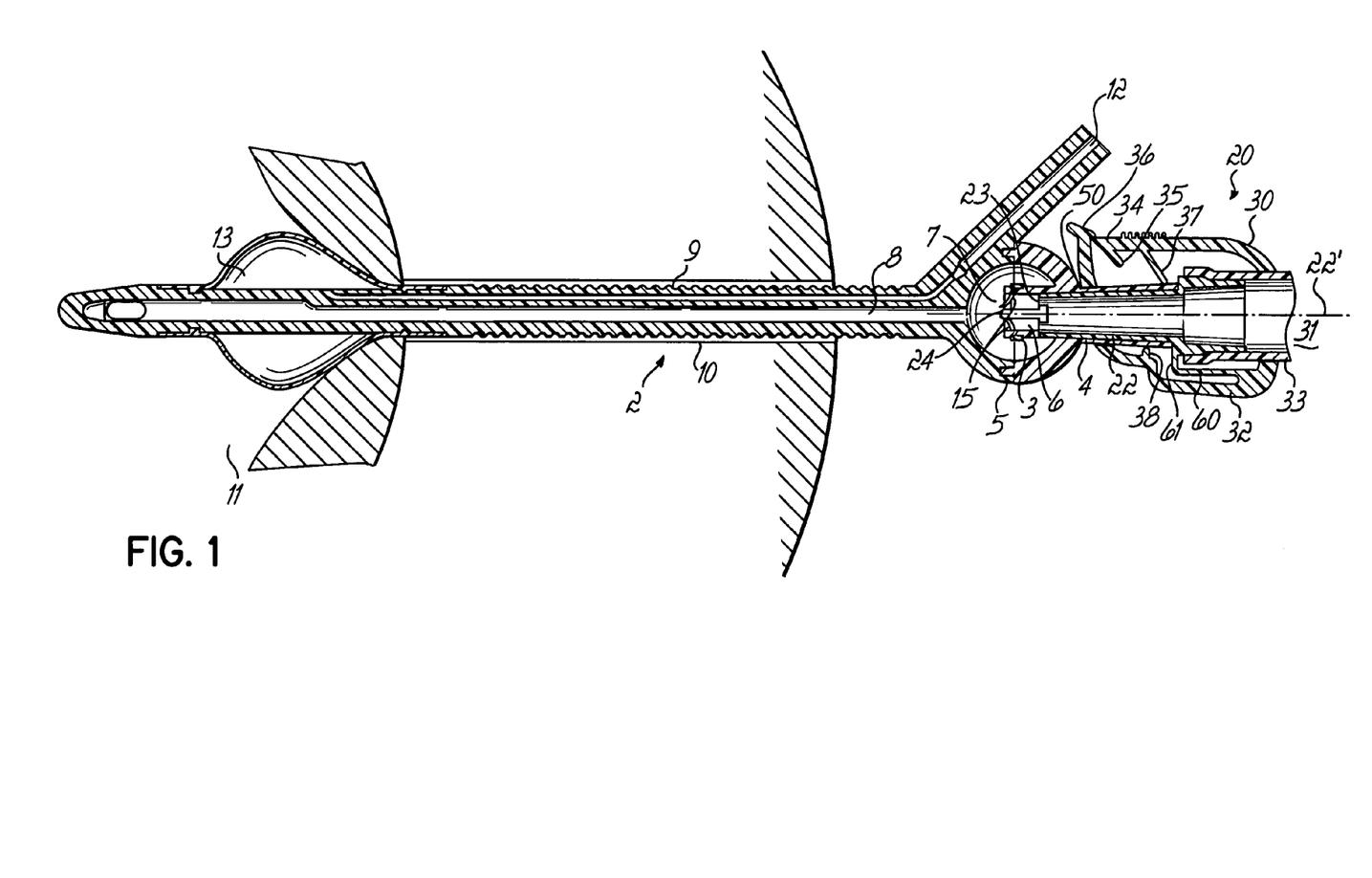
FIG. 1 is a cross-sectional view of an adaptor in accordance with principles of the present invention as inserted within the outlet of a catheter.

With reference to FIG. 1, there is shown a cross-sectional view of an exemplary valved urinary catheter 2, with its normally-closed valve 3 held open by adaptor 20 in accordance with the principles of the present invention such that valved catheter 2 is temporarily transformed into a catheter that permits continuous urine flow therethrough. As will be appreciated, urinary catheter 2 includes a urine outlet tube 4 downstream of valve housing 5 and communicating with the downstream side 6 of valve 3 within valve housing 5. The upstream side 7 of valve 3 communicates through a lumen 8 along catheter body 9 within the urethra 10 of an individual so as to communicate with or into a bladder 11 of the individual (not shown). Catheter 2 may also include one or more further valved lumens 12 used to inflate one or more balloons 13 or the like for holding catheter 2 within the individual's urethra 10. Catheter 2 as shown in FIG. 1 has the valve housing 5 and outlet tube 4 extending outside the urethra 10, although a catheter with the valve within the urethra could also be employed. In either event, valve 3 is of the type that is normally closed, but opens in response to force or pressure externally applied to valve body 5 such as to deform valve 3 to thereby open same to permit the individual to void.

Figure 2:
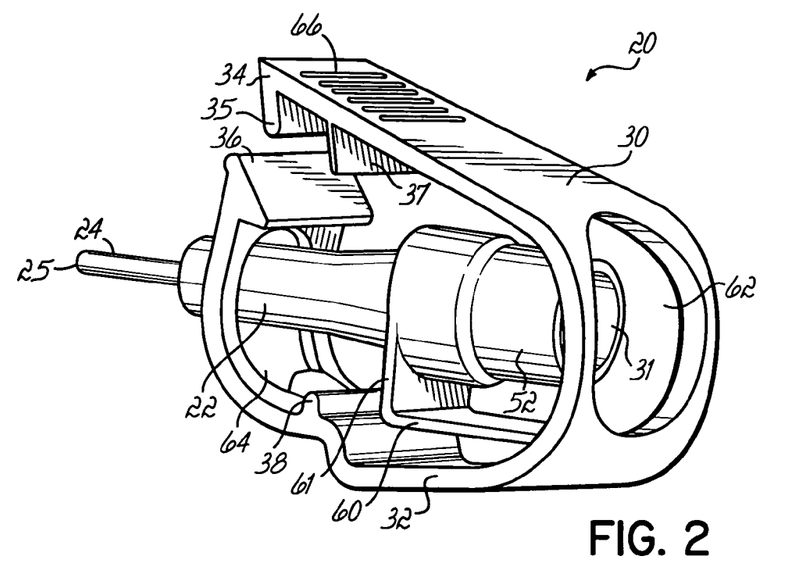
FIG. 2 is a perspective view of the adaptor of FIG. 1.

In order to temporarily transform valved catheter 2 into a catheter that permits continuous urine flow therethrough, adaptor 20 is provided. With reference to FIGS. 1 and 2, adaptor 20 advantageously includes a hollow tube 22 which fits matingly within outlet tube 4 of catheter 2. Extending from upstream end 23 of hollow tube 22 is an actuator member 24 which is sized for urine to flow therearound and into hollow tube 22, such as through end 23 thereof. Instead of having end 23 of tube impact or otherwise deform valve 3, as was conventional of prior hollow tube approaches, the projecting actuator member 24 protrudes into the valve 3 at the downstream side 6 thereof. Actuator member 24 may be a rod as seen in the Figures which has a diameter substantially smaller than the outer diameter of tube 22. This substantially smaller diameter reduces the deformation effect on the valve 3 such that after actuator member 24 is removed, valve 3 will reliably reclose without leakage.

Catheter 2 allows the individual great flexibility in controlling when and how to discharge urine. However, if the individual is to undergo surgery or, for other reasons, becomes immobile, then the normally-closed valve 3 is not entirely beneficial. In those instances, a catheter that allows continuous flow of the urine is more convenient for the individual. Instead of requiring the individual to undergo repeated removal and insertions of various catheters, the adaptor 20 just described may be used to temporarily convert the valved catheter 2 into a continuous flow catheter.

Figure 3:
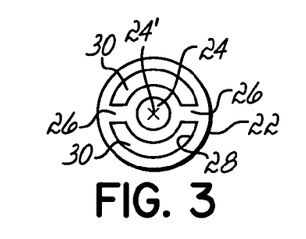
FIG. 3 is a front plan view of the tube and probe of the adaptor of FIG. 2.

Returning to the figures, actuator member 24 may be associated with tube 22 such as by being held to the actuator member 24 so as to be positioned to extend beyond the tube 22. By way of example, as seen in FIG. 3, supporting struts 26 may extend from the inner wall 28 of tube 22 to hold actuator member 24 with a downstream end at or just within upstream end 23 of tube 22. Struts 26 also define large openings 30 through which urine may flow as it passes around actuator member 24 and into tube 22, so as to communicate through tube 22 and out of adaptor 20. The outlet or downstream end 31 of tube 22 may be connected, either permanently or selectively, to a drainage tube 33, which couples to a drainage bag or the like (not shown) for collection and subsequent disposal or other handling, of the urine from the individual.

To create a fluid tight seal between the adaptor 20 and the catheter 2, at least the upstream end 23 of the tube 22 has an outer diameter that is smaller than, but substantially similar to, the inside diameter of the outlet tube 4 so that the adaptor 20 can slide into outlet tube 4. The adaptor tube 22 is substantially cylindrical at its upstream portion and becomes conical so as to taper outwardly towards its downstream portion. This shape helps create a friction fitting when engaging the inside of the outlet tube 4. In this position, the urine cannot flow between the inside of the outlet tube 4 and the outside of the adaptor tube 22; but, instead, flows within the adaptor tube 22. The outlet tube 4 is depicted as having a circular cross-section and the adaptor is shaped accordingly to complement that shape. However, the outlet of the catheter need not be a tube, but an opening, and in any event may have a different cross-sectional profile, such as triangular or some other shape, in which case the adaptor tube 22 would be shaped accordingly so as to create the desired friction fitting.

Thus, when the tube 22 is inserted within the catheter outlet 4, a snug fit is created that prevents urine leakage between the two. Additionally, the actuator member 24 engages the downstream side of the valve 3 so as to deflect the valve 3 into an open position such that urine flows through the valve and around the actuator member 24. Accordingly, fluid is able to flow through the valve 3 but the valve 3 is not grossly deformed or damaged by the tube 22.

The particular adaptor 20 depicted in FIGS. 1 and 2, includes additional features that enhance its ability to remain securely attached to the catheter 2. In particular, a releasable clip consists of two resilient arms 30, 32 that fixedly snap together by engaging the detent 34 of the arm 30 with the latch 36 of the arm 32. When so engaged, one pinch rib 37 pinches down towards the tube 22 and the other pinch rib 38 pinches up towards the tube 22. Thus, when the adaptor 20 is inserted in the catheter 2 and the arms 30, 32 are engaged, the pinch ribs 37, 38 act to hold the outlet tube 4 firmly against the adaptor tube 22. The pinch rib 37 is advantageously angled toward one end, such as the downstream end, and is made more resilient (either by selection of materials or due to its thinness) than the other portions so as to permit greater deflection of this pinch rib 37. As a result, pinch rib 37 operates with a spring-like effect that prevents crushing the outlet tube 4 and also applies a more reliable force on tube 4. To further enhance the operation of the pinch ribs 37, 38, they can be shaped so that their profile matches the outside curvature of the tube 22. Thus, when engaged, more surface area of the pinch ribs 37, 38 will contact the outlet tube 4. The arm 30 and detent 34 extend into a safety rib portion 35. This safety rib 35 acts as a mechanical stop that prevents the arm 30 from being overly compressed towards the tube 22. As a result, over-flexing of the pinch rib 37, and damage thereto and/or to outlet tube 4, is prevented.

In operation, urine communicates from the bladder 11 to the valve 3. As shown, when the tube 22 is inserted within the outlet tube 4, the actuator member 24 engages the valve 3 from the downstream side to cause the valve 3 to open, such as by deflecting the valve walls 15. Urine flows through the now-open valve 3, over the actuator member 24 and towards the inside the tube 22 passing through the openings 30 that are at the base of the actuator member 24 (see FIG. 3). The urine can then travel through the hollow tube 22 of the adaptor 20 towards the downstream end 31.

The depth at which the tube 22 and the actuator member 24 are inserted within the catheter 2 may affect proper operation of the adaptor 20. Accordingly, the resilient arms 30, 32 can be sized and shaped to assist in positioning the adaptor 20. As shown in FIG. 1, the edge of the arm 32 below the latch 36 acts as a protuberance which butts up in contact with the outside of the valve body 5 of catheter 2 as at region 50. This contact between the adaptor 20 and the catheter 2 acts as a positive stop and will not permit the adaptor 20 to be over-inserted into the catheter 2 and valve 3. Over insertion can increase the deflection, or deformation, of the valve 3 or, in the extreme, lead to damage of the valve 3. Different shaped and sized valve bodies are contemplated within the scope of the present invention and, therefore, a variety of functionally equivalent techniques can be used to have the adaptor 20 engage some feature of the catheter 2 so as to indicate when the adaptor 20 is fully inserted and to prevent over-insertion.

By positioning the pinch ribs 37, 38 so that they apply their pinching effect downstream along the tube 22, the individual is given a visual indication that the adaptor 20 may be under-inserted because the pinch ribs 37, 38 will not engage any portion of the outlet tube 4 if the adaptor 20 is not inserted far enough. Thus, the shape and size of the resilient arms 30, 32 and their accompanying features, such as the pinch ribs 37, 38, assist the individual in properly inserting the adaptor 20 within the catheter 2.

From the perspective view of FIG. 2, the two piece support arm 60, 61 may be more easily appreciated than in the view of FIG. 1. The horizontal support arm 60 attaches to the resilient arm 32 and extends upstream. The vertical support arm 61 attaches to an intermediate region of the hollow tube 22. Although FIG. 2 depicts an embodiment of the adaptor 20 that has all features integrally formed, such as would result from thermoplastic injection molding, other embodiments of the present invention contemplate two or more separate pieces assembled together to form the adaptor 20. For example, the resilient arms 30, 32 can be formed separately from an assembly of the actuator member 24, tube 22, and support arms 60, 61. These two assemblies could then be connected together. Alternatively, the resilient arms 30, 32, the support arms 60, 61, and a downstream portion 52 of the tube 22 could be formed integrally and attached to an assembly of the actuator member 24, and the upstream portion of the tube 22. The adaptor 20 is advantageously molded from Profax PF511 Polypropylene thermoplastic; however, other thermoplastic materials can be used such as HDPE, Acetyl, or other medical grade plastic.

As shown, the resilient arms 30, 32 have respective openings 62 and 64. The opening 62 accommodates the downstream end 31 of the adaptor 20 and facilitates attaching a urine discharge device. The opening 64 is near the upstream side of the adaptor 20 and allows the tube 22 to fit inside the outlet tube 4 of the catheter 2 without interfering. Additional features, such as the ribs 66, are also shown in FIG. 2 and can provide tactile assistance to an individual using the adaptor 20.

Figure 4A:
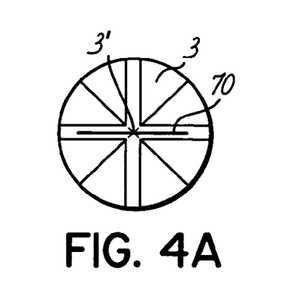
FIGS. 4A and 4B are front views of a duckbill valve in a closed position and an open position, respectively for purposes of explaining the principles of the present invention.
Figure 4B:
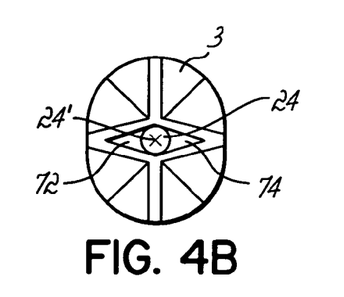

Exemplary embodiments of the present invention are particularly adapted to work with catheters and valves, such as double duckbill valves, that are described in the present Assignee's co-pending patent application Ser. No. 10/000, 276, filed Nov. 2, 2001, the disclosure of which is incorporated herein in its entirety by reference. In general, however, the adaptor 20 herein described can operate with any valved urinary catheter in which the valve can be deformed or deflected from the downstream side so as to open. In particular, FIGS. 4A and 4B illustrate the interaction of the actuator member 24 with such a valve 3 when the adaptor 20 is inserted into the catheter 2. Both of these figures depict the valve 3 as viewed from the bladder end looking downstream towards the outlet tube 4. The valve 3, such as a double duckbill valve, is shown in its closed position in FIG. 4A. As such, the slit 70 is closed and, in this position, can withstand typical urinary fluid pressures without leaking. However, when the adaptor 20 is coupled to the catheter 2, the actuator member 24 engages a portion of the valve 3 from its downstream end to displace the walls 15 so as to cause the slit 70 of the valve 3 to open. Actuator member need not project through the slit 70 to open the valve 3 but may advantageously do so to define fluid flow regions 72, 74 on each side of the actuator member 24.

In the embodiments shown herein, the major axis 22' of tube 22, the major axis 24' of actuator member 24, and centerline 3' of valve 3 are all aligned or coaxial. They need not be, however. For example, the major axis 24' of actuator member 24 could be offset from the major axis 22' of tube 22. Advantageously, however, the axes and centerline would be generally aligned so as to extend generally parallel to one another. Actuator member 24 wold thus be offset from the center of the valve 3 and the slit 70 so that only a single fluid flow region is created as the slit 70 opens.

With the valve 3 held in the open position, any urine on the upstream side of the valve 3 will flow through the fluid flow regions 72, 74 towards and into the tube 22 without requiring manipulation of the valve housing 5. The actuator member 24 of the adaptor 20 does not form a complete sealing relationship with the walls 15 of the valve 3; instead, fluid flows over and around the outside of the actuator member 24 (and also through it if it is hollow). Referring back to the earlier figures, urine will flow through the openings 30, through the tube 22 of the adaptor 20, and out the downstream end 31. In this manner, continuous fluid flow can still be achieved while avoiding the extensive deformation of the valve 3 that results from use of only friction fit tubes to open the valve 3. By minimizing the deformation of the valve 3, it retains its ability to return to the closed position of FIG. 4A without leaking or other degradation when the adaptor 20 is eventually removed. Actuator member 24 of the adaptor 20 does not need to fully penetrate the valve 3 in order to open the valve 3. Instead, by simply applying pressure from the downstream side of the valve 3, the walls 15 are opened as shown in FIG. 4B. Thus, FIG. 1 depicts one alternative in which the actuator member 24 extends entirely through or almost entirely through the walls 15 of the valve 3 and it will be appreciated that actuator member 24 may push on the valve walls 15. By way of example, if the actuator member 24 pushes into the valve 3 at least half the thickness of the valve walls 15, then a fluid path through the valve 3 is formed. Thus, a held-open urine flow path is created whether the actuator member 24 extends through the valve 3 or merely deforms the valve walls 15 from the downstream side.

By way of further example, when actuator member is inserted far enough to create fluid flow regions 72, 74, the slit 70 of the duckbill valve 3 may have a length of approximately 0.180 inches. Knowing the outside diameter of the actuator member 24 will permit calculation of the area of regions 72, 74. If the actuator member 24 has a diameter of 0.055 inches, then each region 72, 74 will have an area of approximately 0.0014 square inches for a total of 0.0028 square inches. Thus, an actuator member 24 having a cross-sectional area of 0.0024 square inches can be used to create a larger, relative fluid path of 0.0028 square inches through the valve 3. For additional fluid flow, the actuator member 24 may be hollow to permit fluid flow though its center as well. For example, the actuator member 24 may have an inner diameter (not shown) of 0.035 inches thereby adding another 0.001 square inches of area through which urine may flow.

Thus, embodiments of the present adaptor 20 can be used to temporarily transform a valved urinary catheter 2 into one that permits continuous fluid flow. In particular, the adaptor 20 is inserted within the discharge tube 4 of the catheter 2 so that an actuator portion, or tip, 24 of the adaptor 20 holds the catheter valve 3 in an open position. However, unlike prior techniques, the embodiments of the present invention described herein minimize the deflection and deformation of the valve 3 caused by the actuator portion 24. Instead of deforming the valve 3 to its largest extent so as to form a fluid-tight seal between the actuator portion 24 and the valve 3, the actuator portion 24 deflects the valve 3 in such a manner as to create a fluid flow path in-between the valve 3 and the actuator portion 24. As a result, urine can flow though the valve 3 towards the adaptor 20 without irreparably damaging the valve 3. One additional benefit of this type of adaptor 20 is that it does not require a specific rotational orientation of the adaptor 20 with respect to the catheter 2 and/or the valve 3 but, instead, can be inserted in any rotational orientation.

While an illustrative embodiment has been described in considerable detail, additional advantages and modifications will readily appear to those skilled in the art. By way of example, the adaptor 20 can be sized and shaped to work with a catheter in which the valve and valve housing are located within the urethra as well. Furthermore, the actuator portion, such as the actuator member 24, can be designed to work with other valves that can be deformed from the downstream side so as to open. Additionally, from the view of FIG. 2, it can be seen that the upstream tip 25 of the actuator member 24 is advantageously hemispherical in shape although it could have other shapes. Similarly, while the actuator member 24 is shown as rod-shaped with a circular cross-section, other rod-shapes are possible such as triangular, oval, and square cross-sections. Additionally, instead of attaching the actuator member 24 with struts 26 to the tube 22, similar results can be attained by other, alternative attaching structures or by tapering the tube 22 to a narrow tip in the upstream direction to engage the valve 3 such that the tip of the tube 22 remains smaller in diameter than both the downstream portion of the tube 22 and the outlet tube 4. Urine flows around the outside of the narrow tip as before and enters the tube 22 downstream of the valve 3, for example, through an aperture or other opening (not shown) located downstream of the valve 3 and on the periphery of the narrow tip. Another alternative is that the tube 22 can be sized to engage over the outlet tube 4 rather than within the tube 4. In that case, the actuator member 24 does not need to project past the upstream end 23 of the tube 22. Additionally, the pinch ribs 37 and 38 may have different shapes and features such as teeth, spikes or other pinning-elements that help secure the adaptor 20 to the catheter 2. The invention in its broader aspects is, therefore, not limited to the specific details, representative apparatus and method, and illustrative examples shown and described. Accordingly, departures may also be made from such details without departing from the spirit or scope of the general invention.

What is claimed is:

1. An adaptor for use with a urinary catheter having a urine lumen extending between a bladder end and a discharge end, a normally closed valve associated with said urine lumen and having a downstream side communicating with said discharge end, the adaptor for holding the valve in an open state comprising:
   a fluid tube sized to sealingly engage said discharge end of said urinary catheter in fluid communication with said downstream side of said valve, and an internal diameter sized for urine to flow therethrough;
   a member associated with the fluid tube and having an external dimension sized to allow urine to flow therearound so as to flow into the fluid tube, the member adapted to engage said valve from said downstream side thereof when the fluid tube is in sealing engagement with said discharge end and to hold said valve open while the fluid tube is sealingly engaged with said discharge end such that urine is to pass through said valve and through the fluid tube; and
   a releasable clip including a portion being movable relative to the fluid tube, the clip being configured to selectively secure the fluid tube in said sealing engagement with said discharge end with movement of the movable clip portion relative to the fluid tube.

2. The adaptor of claim 1, wherein said discharge end of said urinary catheter is tubular and extends downstream from said valve, the fluid tube of the adaptor being sized to engage within said tubular discharge end to thereby sealingly engage therewith.

3. The adaptor of claim 1, the movable clip portion including an arm.

4. The adaptor of claim 1, wherein the releasable clip includes a region adapted to pinch a portion of said tubular discharge end between the releasable clip and a portion of the fluid tube engaged within said tubular discharge end.

5. The adaptor of claim 4, wherein a part of the region, which is in contact with said tubular discharge end, has a contour substantially similar to a contour of said tubular discharge end.

6. The adaptor of claim 1, the member being rod-shaped.

7. The adaptor of claim 1, the member being solid in cross-section.

8. The adaptor of claim 1, the member being hollow in cross-section such that urine also flows therethrough.

9. The adaptor of claim 1, the movable clip portion including a rib.

10. The adaptor of claim 1, wherein the releasable clip further includes:
    a first portion adapted to selectively urge an inner surface of said discharge end against the fluid tube.

11. The adaptor of claim 1, further comprising:
    a protuberance positioned to butt up against a portion of said urinary catheter when the member engages said downstream side of said valve thereby preventing the member from being further inserted into said valve.

12. The adaptor of claim 11, wherein:
    the protuberance is located on the releasable clip.

13. The adaptor of claim 1, wherein the member is sized to pass through said valve.

14. The adaptor of claim 1, wherein the member extends beyond the fluid tube.

15. The adaptor of claim 1, the movable clip portion being configured to engage the discharge end.

16. An adaptor for use with a urinary catheter having a urine lumen extending between a bladder end and a discharge end, a normally closed valve associated with said urine lumen and having a downstream side communicating with said discharge end, the adaptor for holding the valve in an open state comprising:

a fluid tube sized to sealingly engage said discharge end of said urinary catheter in fluid communication with said downstream side of said valve, and an internal diameter sized for urine to flow therethrough;

a member associated with the fluid tube and having an external dimension sized to allow urine to flow therearound so as to flow into the fluid tube, the member adapted to engage said valve from said downstream side thereof when the fluid tube is in sealing engagement with said discharge end and to hold said valve open while the fluid tube is sealingly engaged with said discharge end such that urine is to pass through said valve and through the fluid tube; and a releasable clip adapted to selectively secure the fluid tube in said sealing engagement with said discharge end, wherein the releasable clip includes:

a first portion adapted to selectively urge an inner surface of said discharge end against the fluid tube;

a first resilient arm and a second resilient arm with the fluid tube disposed therebetween; and a flange on the first resilient arm adapted to releasably lock with a detent on the second resilient arm when the arms are urged towards one another.

17. The adaptor of claim 16, wherein:
the first resilient arm includes a first pinch rib adapted to selectively urge a first region of said discharge end against the fluid tube; and
the second resilient arm includes a second pinch fib adapted to selectively urge a second region of said discharge end against the fluid tube.

18. The adaptor of claim 16, wherein:
the first resilient arm includes a safety rib adapted to prevent the first resilient arm from being urged against the fluid tube more than a predetermined amount.

19. An adaptor for use with a urinary catheter having a urine lumen extending between a bladder end and a discharge end, a normally closed valve associated with said urine lumen and having a downstream side communicating with said discharge end, the adaptor for holding the valve in an open state comprising:

a fluid tube sized to sealingly engage said discharge end of said urinary catheter in fluid communication with said downstream side of said valve, and an internal diameter sized for urine to flow therethrough;

a member extending beyond the fluid tube and having an external dimension sized to allow urine to flow therearound so as to flow into the fluid tube, the member adapted to engage said valve from said downstream side thereof when the fluid tube is in sealing engagement with said discharge end and to hold said valve open while the fluid tube is sealingly engaged with said discharge end such that urine is to pass through said valve and through the fluid tube; and a releasable clip including a portion being movable relative to the fluid tube, the clip being configured to selectively secure the fluid tube in said sealing engagement with said discharge end with movement of the movable clip portion relative to the fluid tube.

20. The adaptor of claim 19, wherein said discharge end of said urinary catheter is tubular and extends downstream from said valve, the fluid tube of the adaptor being sized to engage within said tubular discharge end to thereby sealingly engage therewith.

21. The adaptor of claim 20, the movable clip portion including an arm.

22. The adaptor of claim 19, wherein the releasable clip includes a region adapted to pinch a portion of said tubular discharge end between the releasable clip and a portion of the fluid tube engaged within said tubular discharge end.

23. The adaptor of claim 22, wherein a part of the region, which is in contact with said tubular discharge end, has a contour substantially similar to a contour of said tubular discharge end.

24. The adaptor of claim 19, the member being rod-shaped.

25. The adaptor of claim 19, the member being solid in cross-section.

26. The adaptor of claim 19, the member being hollow in cross-section such that urine also flows therethrough.

27. The adaptor of claim 19, the movable clip portion including a rib.

28. The adaptor of claim 27, further comprising:
a protuberance positioned to butt up against a portion of said urinary catheter when the member engages said downstream side of said valve thereby preventing the member from being further inserted into said valve.

29. The adaptor of claim 28, wherein:
the protuberance is located on the releasable clip.

30. The adaptor of claim 19, wherein the releasable clip further includes:
a first portion adapted to selectively urge an inner surface of said discharge end against the fluid tube.

31. The adaptor of claim 19, wherein said member is sized to pass through said valve.

32. The adaptor of claim 19, the movable clip portion being configured to engage the discharge end.

33. An adaptor for use with a urinary catheter having a urine lumen extending between a bladder end and a discharge end, a normally closed valve associated with said urine lumen and having a downstream side communicating with said discharge end, the adaptor for holding the valve in an open state comprising:

a fluid tube sized to sealingly engage said discharge end of said urinary catheter in fluid communication with said downstream side of said valve, and an internal diameter sized for urine to flow therethrough;

a member extending beyond the fluid tube and having an external dimension sized to allow urine to flow therearound so as to flow into the fluid tube, the member adapted to engage said valve from said downstream side thereof when the fluid tube is in sealing engagement with said discharge end and to hold said valve open while the fluid tube is sealingly engaged with said discharge end such that urine is to pass through said valve and through the fluid tube; and a releasable clip adapted to selectively secure the fluid tube in said sealing engagement with said discharge end, wherein the releasable clip includes:

a first portion adapted to selectively urge an inner surface of said discharge end against the fluid tube;

a first resilient arm and a second resilient arm with the fluid tube disposed therebetween; and a flange on the first resilient arm adapted to releasably lock with a detent on the second resilient arm, when the arms are urged towards one another.

34. The adaptor of claim 33, wherein:
the first resilient arm includes a first pinch rib adapted to selectively urge a first region of said discharge end against the fluid tube; and the second resilient arm includes a second pinch rib adapted to urge a second region of said discharge end against the fluid tube.

35. The adaptor of claim 33, wherein:
the first resilient arm includes a safety rib adapted to prevent the first resilient arm from being urged against the fluid tube more than a predetermined amount.

36. An adaptor for use with a fluid catheter having a lumen extending between an upstream end and a downstream end, a normally closed valve associated with said fluid lumen and having a downstream side communicating with said downstream end, the adaptor for holding the valve in an open state comprising:
a fluid tube sized to sealingly engage said downstream end of said fluid catheter in fluid communication with said downstream side of said valve, and an internal diameter sized for fluid to flow therethrough;
a member associated with the fluid tube and having an external dimension sized to allow fluid to flow therearound so as to flow into the fluid tube, the member adapted to engage said valve from said downstream side thereof when the fluid tube is in sealing engagement with said downstream end and to hold said valve open while the fluid tube is sealingly engaged with said downstream end such that fluid is to pass through said valve and through the fluid tube; and
a releasable clip including a portion being movable relative to the fluid tube, the clip being configured to selectively secure the fluid tube in said sealing engagement with said downstream end with movement of the movable clip portion relative to the fluid tube.

37. The adaptor of claim 36, wherein said downstream end of said fluid catheter is tubular and extends downstream from said valve, the fluid tube of the adaptor being sized to engage within said tubular downstream end to thereby sealingly engage therewith.

38. The adaptor of claim 36, the member being solid in cross-section.

39. The adaptor of claim 36, the member being hollow in cross-section such that fluid also flows therethrough.

40. The adaptor of claim 36, the movable clip portion including an arm.

41. The adaptor of claim 36, further comprising:
a protuberance positioned to butt up against a portion of said fluid catheter when the member engages said downstream side of said valve thereby preventing the member from being further inserted into said valve.

42. The adaptor of claim 36, wherein the member is sized to pass through said valve.

43. The adaptor of claim 36, wherein the member extends beyond the fluid tube.

44. The adaptor of claim 36, the movable clip portion including a rib.

45. The adaptor of claim 36, the movable clip portion being configured to engage the downstream end.

46. An adaptor for use with a fluid catheter having a lumen extending between an upstream end and a downstream end, a normally closed valve associated with said fluid lumen and having a downstream side communicating with said downstream end, the adaptor for holding the valve in an open state comprising:
a fluid tube sized to sealingly engage said downstream end of said fluid catheter in fluid communication with said downstream side of said valve, and an internal diameter sized for fluid to flow therethrough;
a member extending beyond the fluid tube and having an external dimension sized to allow fluid to flow therearound so as to flow into the fluid tube, the member adapted to engage said valve from said downstream side thereof when the fluid tube is in sealing engagement with said downstream end and to hold said valve open while the fluid tube is sealingly engaged with said downstream end such that fluid is to pass through said valve and through the fluid tube; and
a releasable clip including a portion being movable relative to the fluid tube, the clip being configured to selectively secure the fluid tube in said sealing engagement with said downstream end with movement of the movable clip portion relative to the fluid tube.

47. The adaptor of claim 46, wherein said downstream end of said fluid catheter is tubular and extends downstream from said valve, the fluid tube of the adaptor being sized to engage within said tubular downstream end to thereby sealingly engage therewith.

48. The adaptor of claim 46, the member being solid in cross-section.

49. The adaptor of claim 46, the member being hollow in cross-section such that fluid also flows therethrough.

50. The adaptor of claim 46, the movable clip portion including an arm.

51. The adaptor of claim 46, further comprising:
a protuberance positioned to butt up against a portion of said fluid catheter when the member engages said downstream side of said valve thereby preventing the member from being further inserted into said valve.

52. The adaptor of claim 46, wherein the member is sized to pass through said valve.

53. The adaptor of claim 52, the movable clip portion being configured to engage the discharge end.

54. The adaptor of claim 46, the movable clip portion including a rib.

55. The adaptor of claim 46, the movable clip portion being configured to engage the downstream end.

56. An adaptor for use with a urinary catheter having a urine lumen extending between a bladder end and a discharge end, a normally-closed valve associated with said urine lumen and having a downstream side communicating with said discharge end, the adaptor for holding the valve in an open state comprising:
a rigid fluid tube sized to sealingly engage said discharge end of said urinary catheter for urine flow therethrough; and
a releasable clip external to the fluid tube and including a portion movable relative to the fluid tube, the clip being configured to selectively secure the fluid tube in said sealing engagement with said discharge end with movement of the movable clip portion relative to the fluid tube, the fluid tube projecting through an aperture of the releasable clip spaced from a peripheral edge of the aperture.

57. The adaptor of claim 56, wherein the releasable clip further includes:
a first portion adapted to selectively urge a portion of the discharge end against the fluid tube.

58. The adaptor of claim 56, wherein the adaptor further includes:
a member having an external dimension sized to allow urine to flow therearound and into the fluid tube, the member adapted to engage said downstream side of said valve when the fluid tube is in sealing engagement with said discharge end and hold said valve open by internal actuation while the fluid tube is sealingly engaged with said discharge end such that urine is to pass through said valve and through the fluid tube.

59. The adaptor of claim 58, wherein the releasable clip further includes:
a protuberance positioned to butt up against a portion of said urinary catheter when the member engages said downstream side of said valve thereby preventing the member from being further inserted into said valve.

60. The adaptor of claim 56, wherein the fluid tube has an external diameter sized to fit within said discharge end of said urinary catheter in fluid communication with said downstream side of said valve, and an internal diameter sized for urine to flow therethrough.

61. An adaptor for use with a urinary catheter having a urine lumen extending between a bladder end and a discharge end, a normally-closed valve associated with said urine lumen and having a downstream side communicating with said discharge end, the adaptor for holding the valve in an open state comprising:
a rigid fluid tube sized to sealingly engage said discharge end of said urinary catheter for urine flow therethrough; and
a releasable clip external to the fluid tube adapted to selectively secure the fluid tube in said sealing engagement with said discharge end, wherein said releasable clip includes:
a first portion adapted to selectively urge a portion of the discharge end against the fluid tube;
a first resilient arm and a second resilient arm with the fluid tube disposed therebetween; and
a flange on the first resilient arm adapted to releasably lock with a detent on the second resilient arm, when the arms are urged towards one another.

62. The adaptor of claim 61, wherein:
the first resilient arm includes a first pinch rib adapted to selectively urge a first region of said discharge end against the fluid tube; and
the second resilient arm includes a second pinch rib adapted to selectively urge a second region of said discharge end against the fluid tube.

63. An adaptor comprising:
a fluid tube, the fluid tube having a downstream end and an upstream end;
a rigid valve opening member associated with, and held in fixed spatial relationship to, the fluid tube; and
a clip fixedly coupled with the fluid tube; the clip having a first resilient arm with a first opening through which the valve opening member extends, and a second resilient arm with a second opening accommodating said downstream end, and the first resilient arm and the second resilient arm positioned with the fluid tube disposed therebetween.

64. The adaptor of claim 63 further comprising a safety rib on the second resilient arm and extending towards the fluid tube, the safety rib being adapted to prevent the second resilient arm from being urged against the fluid tube more than a predetermined amount.

65. The adaptor of claim 63 further comprising a resilient rib on one of the resilient arms and extending towards the fluid tube, the resilient rib being adapted to communicate with the fluid tube when the clip is in a closed position.

66. The adaptor of claim 65, the resilient rib being disposed at an angle.

67. The adaptor of claim 63, wherein the valve opening member extends beyond the fluid tube upstream therefrom.

68. An adaptor comprising:
a fluid tube, the fluid tube having a downstream end and an upstream end;
a rigid valve opening member extending beyond, and held in fixed spatial relationship to, the fluid tube upstream therefrom; and
a clip fixedly coupled with the fluid tube; the clip having a first resilient arm with a first opening through which the valve opening member extends, and a second resilient arm with a second opening accommodating said downstream end, and the first resilient arm and the second resilient arm positioned with the fluid tube disposed therebetween.

69. The adaptor of claim 68 further comprising a safety rib on the second resilient arm and extending towards the fluid tube, the safety rib being adapted to prevent the second resilient arm from being urged against the fluid tube more than a predetermined amount.

70. The adaptor of claim 68 further comprising a resilient rib on one of the resilient arms and extending towards the fluid tube, the resilient rib being adapted to communicate with the fluid tube when the clip is in a closed position.

71. The adaptor of claim 70, the resilient rib being disposed at an angle.

72. A catheter arrangement comprising:
a catheter comprising a fluid lumen extending between an upstream end and a downstream end, a normally-closed valve associated with said fluid lumen and having a downstream side in communication with said downstream end, and
an adaptor, comprising:
a fluid tube sized to sealingly engage the downstream end of the catheter in fluid communication with the downstream side of the valve for fluid to flow therethrough;
a member associated with the fluid tube and having an external dimension sized to allow fluid to flow therearound so as to flow into the fluid tube, the member adapted to engage the valve from the downstream side thereof when the fluid tube is in sealing engagement with the downstream end of the catheter and to hold the valve open while the fluid tube is sealingly engaged with the downstream end such that fluid is to pass through the valve and through the fluid tube; and
a releasable clip including a portion being movable relative to the fluid tube, the clip being configured to selectively secure the fluid tube in said sealing engagement with said downstream end with movement of the movable clip portion relative to the fluid tube.

73. The arrangement according to claim 72, wherein the valve includes a duck-bill valve.

74. The arrangement according to claim 73, wherein the member further includes:
a rod having a major axis substantially aligned with a major axis of the downstream end of the fluid lumen and is positioned within the duck-bill valve, when the member engages the valve, so as to form a respective open region on each side of the rod bounded by the duck-bill valve.

75. The arrangement according to claim 74, wherein a combined cross-sectional area of the respective open regions is larger than a cross-sectional area of the rod.

76. The arrangement according to claim 74, wherein the rod comprises a hollow central region along its major axis whereby fluid flows out of the catheter through the hollow central region.

77. The arrangement according to claim 72, wherein the member extends upstream beyond the fluid tube.

78. The arrangement according to claim 77, wherein the valve includes a duck-bill valve.

79. The arrangement according to claim 78, wherein the member further includes:
- a rod having a major axis substantially aligned with a major axis of the downstream end of the fluid lumen and is positioned within the duck-bill valve, when the member engages the valve, so as to form a respective open region on each side of the rod bounded by the duck-bill valve.

80. The arrangement according to claim 79, wherein a combined cross-sectional area of the respective open regions is larger than a cross-sectional area of the rod.

81. The arrangement according to claim 79, wherein the rod comprises a hollow central region along its major axis whereby fluid flows out of the catheter through the hollow central region.

82. The adaptor of claim 72, the movable clip portion being configured to engage the downstream end.

83. A catheter arrangement comprising:
- a catheter comprising a fluid lumen extending between an upstream end and a downstream end, a normally-closed valve associated with said fluid lumen and having a downstream side in communication with said downstream end, and
- an adaptor, comprising:
  - a fluid tube sized to sealingly engage the downstream end of the catheter in fluid communication with the downstream side of the valve for fluid to flow therethrough;
  - a member extending beyond the fluid tube upstream therefrom and having an external dimension sized to allow fluid to flow therearound so as to flow into the fluid tube, the member adapted to engage the valve from the downstream side thereof when the fluid tube is in sealing engagement with the downstream end of the catheter and to hold the valve open while the fluid tube is sealingly engaged with the downstream end such that fluid is to pass through the valve and through the fluid tube; and
  - a releasable clip including a portion being movable relative to the fluid tube, the clip being configured to selectively secure the fluid tube in said sealing engagement with said downstream end with movement of the movable clip portion relative to the fluid tube.

84. The adaptor of claim 83, the movable clip portion being configured to engage the downstream end.

* * * * *

UNITED STATES PATENT AND TRADEMARK OFFICE
CERTIFICATE OF CORRECTION

PATENT NO. : 7,306,586 B2 Page 1 of 1
APPLICATION NO. : 10/749063
DATED : December 11, 2007
INVENTOR(S) : Spencer W. Beaufore and Glenn D. Brunner It is certified that error appears in the above-identified patent and that said Letters Patent is hereby corrected as shown below:

Claim 17, Column 9, line 31, "a second pinch fib" should be -- a second pinch rib --

Signed and Sealed this

Twenty-first Day of October, 2008

JON W. DUDAS
*Director of the United States Patent and Trademark Office*